United States Patent [19]

Gaertner

[11] 4,413,125

[45] Nov. 1, 1983

[54] α-HYDROXY PHOSPHONATES

[75] Inventor: Van R. Gaertner, Ballwin, Mo.

[73] Assignee: Monsanto Company, St. Louis, Mo.

[21] Appl. No.: 279,371

[22] Filed: Jul. 1, 1981

[51] Int. Cl.$^3$ .............................. C07F 9/40; C07F 9/65
[52] U.S. Cl. ...................................... 546/22; 260/944; 260/945; 260/948; 260/949; 260/952; 260/950; 260/953; 260/970; 71/86; 71/87
[58] Field of Search ............... 260/953, 952, 948, 944, 260/949; 546/22

[56] References Cited

U.S. PATENT DOCUMENTS 2,579,810 12/1951 Fields ................................. 260/953
3,649,619 3/1972 Pollack et al. ...................... 260/953

*Primary Examiner*—Anton H. Sutto
*Attorney, Agent, or Firm*—Gordon F. Sieckmann

[57] ABSTRACT

This invention relates to α-hydroxy phosphonates which are useful as herbicides. More particularly, this invention relates to α-hydroxy phosphonates a process for preparing the same, herbicidal use thereof, and to herbicidal methods and compositions employing the same.

10 Claims, No Drawings

α-HYDROXY PHOSPHONATES

This invention relates to α-hydroxy phosphonates which are useful as herbicides. More particularly, this invention relates to α-hydroxy phosphonates a process for preparing the same, herbicidal use thereof, and to herbicidal methods and compositions employing the same.

U.S. Pat. No. 2,579,810 issued to Ellis K. Fields on Dec. 25, 1951 discloses hydroxymethyl phosphonic esters of the formula

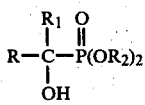

wherein R, $R_1$, and $R_2$ of Fields may be the same or different radicals including alkyl, aryl, aralkyl, cycloalkyl, and heterocyclic radicals, as well as such radicals containing substituents such as halogen, nitro, amino, hydroxy, alkoxy, mercapto, carbonyl, carboxy, thiocyano, and the like. The Fields compounds are said to be useful as intermediates for resins, plasticizers for resins, pharmaceuticals, insecticides, bactericides, and fungicides, and in perfume compositions.

U.S. Pat. No. 3,385,801 issued to Birum et al, on May 28, 1968 discloses -hydroxy phosphonates of the formula

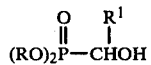

wherein each R of Birum et al is an alkyl group having from 1 to about 4 carbon atoms and $R^1$ of Birum et al is either hydrogen or an alkyl group of from 1 to about 3 carbon atoms. The compounds are said to be useful to impart flame resistance to polyurethanes, and are incorporated into the reactant mixture for making the polyurethane.

U.S. Pat. No. 2,758,971 issued to Louis A. Mikeska on Aug. 14, 1956 discloses esters of hydroxy phosphonic acids of the following formula

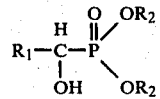

wherein $R_1$ of Mikeska is selected from the group consisting of hydrogen and hydrocarbon radicals having from 1 to 12 carbon atoms, $R_2$ of Mikeska is selected from the group consisting of hydrogen, hydrocarbon radicals, sulfurized hydrocarbon radicals, and alkylphenol sulfide radicals having from 1 to 30 carbon atoms, at least one S being an organic group. The esters are said to be useful in lubricating oils to improve the properties of the oils.

U.S. Pat. No. 3,189,635 issued to Charles H. Tieman on June 15, 1965 discloses hydroxy phosphonate esters of the formula

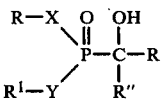

wherein R, $R^1$ and R" of Tieman are each a lower molecular weight hydrocarbon or lower molecular weight substituted hydrocarbon group, $R^o$ of Tieman is a lower molecular weight hydrocarbon or lower molecular weight substituted hydrocarbon group bonded to the carbonyl carbon atom by an aliphatic carbon atom which also is bonded to at least one hydrogen atom.

X and Y of Tieman are disclosed as —O— as well. The Tieman esters are said to be useful as special-purpose insecticides.

The α-hydroxy phosphonate compounds of the present invention are represented by the formula

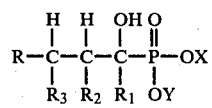

wherein X and Y are each independently selected from the group consisting of lower alkyl, halo lower alkyl, phenyl, or benzyl; $R_1$, $R_2$ and $R_3$ are each independently selected from the group consisting of hydrogen, lower alkyl, or phenyl; R is a —Z—$R_4$ group wherein Z is oxygen or sulfur, and $R_4$ is lower alkyl, aryl or substituted lower alkyl or R is a

group wherein Z' is nitrogen and $R_5$ is lower alkyl, or substituted lower alkyl and $R_6$ is lower alkyl or hydrogen, or R is piperidinyl or R is —CH($C_2H_5O_2C$)$_2$.

The term "lower alkyl" includes alkyl radicals having up to 4 carbon atoms in a straight or branched chain such as methyl, ethyl, propyl, isopropyl, butyl, isobutyl, sec-butyl and t-butyl.

The term "aryl" includes aryl groups of 6 to 12 carbon atoms and includes phenyl, biphenylyl, naphthyl; and substituted phenyl, biphenylyl and naphthyl and includes methylphenyl, ethylphenyl, propylphenyl; halophenyl such as chlorophenyl, bromophenyl, iodophenyl, fluorophenyl; and lower alkoxyphenyl such as methoxyphenyl, ethoxyphenyl, propoxyphenyl, mixtures thereof, and the like.

The term "substituted lower alkyl" includes the aforedefined lower alkyl groups having substituents selected from the group consisting of halogen and lower alkoxy.

The term "lower alkoxy" includes groups having a combination of oxygen with a group herein aforedefined as "lower alkyl".

Groups illustrative of halogen include chlorine, bromine, iodine and fluorine while groups illustrative of lower alkoxy include methoxy, ethoxy, propoxy, butoxy and the like.

In accordance with this invention, in a first step, compounds of formula (I) are prepared by a process comprising (a) reacting a compound of the formula

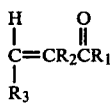

(II)

wherein $R_1$, $R_2$ and $R_3$ are as aforedefined with a nucleophile of the formula $$ZH \qquad (III)$$

to form an intermediate compound of the formula

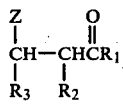

(IV)

wherein $R_1$, $R_2$ and $R_3$ are as aforedefined and ZH is a nucleophile selected from the group consisting of amines, alcohols, thiols and active hydrogen compounds hereinafter discussed in detail.

In a second step (b), said intermediate compound of formula (IV) is reacted (preferably in situ) with a disubstituted phosphite of the formula

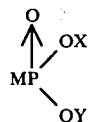

(V)

wherein X and Y are as aforedefined, and M is hydrogen or an alkali metal such as sodium or potassium to form a compound of formula (I). Illustrative disubstituted phosphites include di(lower alkyl)phosphites such as diethyl phosphite, dimethyl phosphite, and dipropyl phosphite although diethyl phosphite is preferred disubstituted phosphite.

Illustrative compounds of formula (II) include acrolein, methacrolein, methylvinyl ketone while acrolein is preferred.

The term "amine" includes compounds of the formula

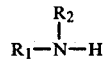

(VI)

wherein $R_1$ and $R_2$ are selected from the group consisting of hydrogen and lower alkyl.

Examples of suitable amines include those amines containing not more than two amine groups, for example, mono and di-(lower alkyl)amine, (loweralkylene)-diamines, mono lower alkanolamine, di(lower alkanol)amine and mixtures thereof.

Suitable mono and di-(lower alkyl)amines include methylamine, ethylamine, n-propylamine, isopropylamine, n-butylamine, isobutylamine, sec-butylamine, dimethylamine, diethylamine, di-n-propylamine, diisopropylamine, dibutylamine, and mixed di-alkylamines such as methylethylamine, n-propylmethylamine, methylbutylamine, mixtures thereof and the like.

Suitable lower alkylenediamines include ethylenediamine, propylenediamine mixtures thereof and the like.

Suitable mono lower alkanolamines include ethanolamine, propanolamine and butanolamine. Suitable di(-lower alkanol)amines include diethanolamine, dipropanolamine, and bibutanolamine.

Suitable alcohols and thio compounds which may be employed in the process of this invention include those compounds of the formula $$R-ZH \qquad (VII)$$

wherein Z is oxygen or sulfur and R is lower alkyl or aryl.

Suitable alcohols include n-propyl alcohol, iospropyl alcohol, methanol, ethanol, isobutanol, sec-butanol, tert-butyl alcohol, n-hexyl alcohol, n-octyl alcohol, mixtures thereof and the like.

Preferred alcohols include methanol, ethanol and isobutanol.

Illustrative thio compounds which may be employed in practicing this invention include lower alkyl mercaptans including methyl mercaptan, ethylmercaptan, n-butyl mercaptan, n-amyl mercaptan, n-heptylmercaptan, mixtures thereof and the like.

Preferable lower alkyl mercaptans include methyl mercaptan, n-butyl mercaptan, n-amyl mercaptan and isopropyl mercaptan.

Other illustrative thio compounds which may be employed in practicing this invention include aryl mercaptans such as thiophenols or substituted thiophenols for example chlorothiophenol.

Preferred aryl mercaptans include thiophenol and chlorothiophenol.

Other thio compounds acceptable in practicing the process of this invention include sodium, potassium and lithium mercaptides.

Other compounds which may be suitably employed as a nucleophile in practicing the process of this invention, include active hydrogen compounds.

The term "active hydrogen compound" includes those compounds which are capable of forming a carbanion and include di(lower alkyl) malonates of the formula $$(R'O_2C)_2CH_2 \qquad (VIII);$$

lower alkyl acetoacetates of the formula $$R''O_2CCH_2COCH_3 \qquad (IX);$$

lower alkyl cyanoacetates of the formula $$R'''O_2CCH_2CN \qquad (X);$$

lower alkyl monoalkylated forms of lower alkyl acetoacetates of the formula $$R''O_2CCHCOCH_3; \qquad (XI)$$
$$\quad\; |$$
$$\quad\; R^y$$

diketones of the formula $$R^yCOCH_2COR''' \qquad (XII);$$

cyanomethylketone; 2-lower alkyl malonate esters of the formula $$(R''''O_2C)_2CH; \qquad (XIII)$$
$$\quad\; |$$
$$\quad\; R'^x$$

wherein R', R'', R''', R'$^v$, R$^v$, R$^{v'}$, R$^{v''}$, R$^{v'''}$ and R'$^x$ are each independently lower alkyl.

The temperature of the reaction is in the range from about 0° C. to about 100° C. and is preferably from about 10° C. to about 40° C. although greater or lesser temperatures may be employed if desired.

The pressure of the reaction may be sub-, super-, or atmospheric if desired although atmospheric pressure is preferred.

The molar ratio of compounds of formula (I) to said nucleophile is in the range from about 0.5 to about 10 and is preferably from about 1 to about 2.

The molar ratio of compounds of formula (IV) to said intermediate compounds of formula (VII) is in the range from about 1 to about 20 and is preferably from about 1 to about 5.

Those of skill in the art will recognize that said intermediate compound is advantageously not required to be isolated in practicing the process of this invention, although isolation may be practiced, if desired.

Typically for best resuts a catalyst is employed in reacting compounds of formula (I) with a nucleophile of formula (III) when the nucleophile is an aforedefined alcohol, an active hydrogen compound or a thio compound.

Compounds which may be suitably employed as catalyst in the process of this invention include tri(lower alkyl)amines such as trimethylamine, triethylamine, tributylamine, pyridine, picolines, alkoxides, mixtures thereof and the like. A preferred tri(lower alkyl)amine is triethylamine.

Typical alkoxides useful as catalysts in this invention include alkali metal alkoxides such as sodium methoxide, sodium ethoxide, sodium propoxide, sodium butoxide, potassium ethoxide, potassium propoxide, potassium butoxide, mixtures thereof and the like.

Those of skill in the art will recognize that if significant moisture is present during the reaction of compounds of formula (IV) with compounds of formula (III) that the reaction, for best results, should be conducted in presence of a strong base.

Typical acceptable strong bases include sodium, lithium and potassium alkoxides in alcohol solution, sodium hydroxide, potassium hydroxide, amines such as tri(lower alkyl)amines such as trimethylamine, triethylamine, tripropylamine, tributylamine, mixtures thereof and the like and compounds of the formula $$\underset{\text{MP(OR}^x)_2}{\overset{\text{O}}{\|}} \quad \text{(XIV)}$$

wherein M is an alkali metal such as sodium or potassium and R$^x$ is lower alkyl.

Illustrative alkali metal compounds of formula (XIV) include sodium diethyl phosphites, potassium diethyl phosphite, sodium dipropyl phosphite, potassium diethyl phosphite, sodium dibutyl phosphite, potassium dibutyl phosphite.

The following examples are presented to define the process of the invention more completely without any intention of being limited thereby. All examples (1–16) are illustrative of an insitu procedure wherein the intermediate product resulting from a reaction of a compound of formula (II) and a nucleophile of formula (II) is not recovered prior to reaction with a compound of formula (III). All parts and percentages are by weight, unless otherwise specified.

EXAMPLE 1

In a first step, 10.4 g (0.100 mole) of n-amyl mercaptan was weighed into a 500 ml 4-neck round-bottom flask fitted with stirrer, thermometer, condenser with Drierite tube, and addition funnel with nitrogen inlet. Triethylamine (0.5 g) was added as a catalyst with stirring and the mixture cooled to 20° C. in an ice bath, then 5.6 g of acrolein in 20 ml of benzene as a solvent was added dropwise, with cooling to maintain the temperature in the range 15°–25° C. After completion of the addition, mechanical stirring was continued, without cooling, at 20°–25° C. for 20 minutes.

In a second step, to the mixture of the first step was added at once 14 g of diethyl phosphite, followed by a first 0.5 g triethylamine addition. No temperature exotherm being noted, 0.5 g of 1 M sodium ethoxide solution in ethanol was added, resulting in a temperature exotherm from a temperature of 25° C. to a temperature of 31° C. A second 0.5 g of triethylamine was added which initiated a stronger temperature exotherm from 30° C. to 51° C. but a third 0.5 g sodium ethoxide addition gave no further temperature effect. The mixture was stirred and allowed to cool 30 minutes.

Following rotoevaporation to remove the benzene solvent, the residual oil was distilled in a Smith molecular still, distillate being collected at a wall temperature of 157°–163° C. and a vacuum of 17–28μ. (1 micron, μ, equal 10$^{-3}$ mm mercury); combined distillate, 23.9 g (80% yield). Redistillation in a small Hickman molecular still gave a purified compound, phosphonic acid, diethyl ester, [1-hydroxy-3-(pentylthio)-propyl-.] 145°–150°/4–3μ; n$_D^{22}$ 1.4722. Analysis for sulfur gave 10.56%; C$_{12}$H$_{27}$O$_4$PS requires 10.75% sulfur.

EXAMPLES 2–7

Other 3-thio-1-hydroxypropanephosphonate ester products of Table I were prepared by 1,4-additions of thiols to α,β-unsaturated carbonyl compounds, as a first step, followed by addition of diethyl phosphite to the carbonyl group following the procedure of Example 1 as a second step. However, triethylamine and sodium ethoxide were the catalysts employed in the first and second steps, respectively for each example.

TABLE I

| Ex. No. | Compound Of Formula (I) | Compound Of Formula (II) | Product Structure | Mol. Dist. Refr. Index | Analyses Calculated | Found |
|---|---|---|---|---|---|---|
| 2 | Acrolein | Thiophenol | C$_6$H$_5$SCH$_2$CH$_2$CHPO$_3$Et$_2$<br>\|<br>OH | 140–145°/20–30μ<br>n$_D^{20}$1.5272 | P, 10.18<br>S, 10.54 | 10.04<br>10.29 |
| 3 | Acrolein | n-Heptyl mercaptan | n-C$_7$H$_{15}$SCH$_2$CH$_2$CHPOEt$_2$<br>\|<br>OH | 140–150°/20–45μ<br>n$_D^{26}$1.4687 | P, 9.49<br>S, 9.82 | 9.88<br>10.18 |

TABLE I-continued

| | | | | | | |
|---|---|---|---|---|---|---|
| 4 | Acrolein | 2-Mercaptoethanol | HOCH$_2$CH$_2$SCH$_2$CH$_2$CHPO$_3$Et$_2$<br>\|<br>OH | 145–150°/20–30μ<br>$n_D^{20}$1.4893 | P, 11.37<br>S, 11.78 | 11.73<br>12.01 |
| 5 | Acrolein | 2-Propanethiol | (CH$_3$)$_2$CHSCH$_2$CH$_2$CHPO$_3$Et$_2$<br>\|<br>OH | 125–135°/20–40μ<br>$n_D^{20}$1.4729 | P, 11.46<br>S, 11.86 | 11.13<br>11.25 |
| 6 | Methacrolein | n-Propyl mercaptan | n-C$_3$H$_7$SCH$_2$CH CHPO$_3$Et$_2$<br>\| \|<br>CH$_3$ OH | 120°/15μ<br>$n_D^{20}$1.4783 | P, 10.89<br>S, 11.28 | 10.97<br>11.70 |
| 7 | Methyl vinyl ketone | n-Propyl mercaptan | CH$_3$<br>\|<br>n-C$_3$H$_7$SCH$_2$CH$_2$C—PO$_3$Et$_2$<br>\|<br>OH | 133–136°/25–30μ<br>$n_D^{20}$1.4729 | P, 10.89<br>S, 11.28 | 9.98<br>11.09 |

| Ex. No. | Product Name |
|---|---|
| 2 | Phosphonic acid, diethyl ester, [1-hydroxy-3-(phenylthio) propyl]-, |
| 3 | Phosphonic acid, diethyl ester, [1-hydroxy-3-(heptylthio)propyl]-, |
| 4 | Phosphonic acid, diethyl ester, [1-hydroxy-3-(2-hydroxyethylthio)propyl]-, |
| 5 | Phosphonic acid, diethyl ester, [1-hydroxy-3-(isopropylthio)-propyl]-, |
| 6 | Phosphonic acid, diethyl ester, [1-hydroxy-2-methyl-3-(propylthio)propyl]-, |
| 7 | Phosphonic acid, diethyl ester, [1-hydroxy-1-methyl-3-(propylthio)propyl]-, |

EXAMPLE 8

In a first step, methyl vinyl ketone, 7.0 g (0.100 mole), was dissolved in 50 ml benzene and, at 23° C., 12.8 g (0.200 mole) of 70% aqueous ethylamine as a catalyst added with stirring, causing a slow exotherm to 44° C. After cooling, in a second step 14.0 g diethyl phosphite was added at once, to the solution of the first step accompanied by an exotherm to 36° C. then slowly to 42° C. with no cooling. The mixture was heated briefly to reflux, then concentrated by rotoevaporation. The dark residual oil was distilled in a Smith molecular still at 138°–146°/10–200μ, giving an oily product; phosphonic acid, [3-(ethylamino)-1-hydroxy-1-methylpropyl]-, diethyl ester; $n_D^{22}$ 1.4637. C$_{10}$H$_{24}$NO$_4$P requires N, 5.53% and P, 12.23%; the experimental data were N, 5.21%; P, 11.57%. In this example, the reacting ethylamine charged in 100% excess in a first step served as a catalyst for both step one and step two of the example.

Equimolar amounts of reactants were employed with sodium ethoxide as a catalyst in the following Examples 9–14.

EXAMPLE 9

In a first step, to a cooled solution of 9.75 ml (0.100 mole) piperidine in 50 ml ethanol (solvent) was added 6.7 g acrolein slowly with stirring, then in a second step 12.9 ml (0.100 mole) diethyl phosphite was added at once to the solution of the first step. Finally, sodium ethoxide (as a catalyst) in ethanol was added. After being allowed to stand 3 days at a temperature of 25° C., the mixture was rotoevaporated and the residual oil distilled in the Smith still, at 140°–145° C./20–35μ. The yellow oily product phosphonic acid, diethyl ester, 1-hydroxy-3-piperidinopropyl weighed 16 g (55% yield); $n_D^{20}$ 1.4739. Analyses gave P, 10.78% and N, 4.43%; C$_{12}$H$_{26}$NO$_4$P requires P, 10.56 and N, 4.77%.

Other 3-amino-1-hydroxypropanephosphonates of following Examples (10–14) were similarly prepared as shown in Table II. Diethyl phosphite was employed in Examples 10–13 while dibenzyl phosphite was employed in Example 14.

TABLE II

| Ex. No. | Compound Of Formula (I) | Compound Of Formula (II) | Product Structure | Mol Dist.<br>Refr. Index | Analyses Calculated | Found |
|---|---|---|---|---|---|---|
| 10 | Acrolein | Diethylamine | (C$_2$H$_5$)$_2$NCH$_2$CH$_2$CHPO$_3$Et$_2$<br>\|<br>OH | 125–140°/20–75μ<br>$n_D^{20}$1.4553 | N, 5.24<br>B, 11.59 | 5.15<br>11.93 |
| 11 | Acrolein | t-amylamine | CH$_3$<br>\|<br>C$_2$H$_5$C—NHCH$_2$CH$_2$CHPO$_3$Et$_2$<br>\| \|<br>CH$_3$ OH | 93–100°/12μ<br>$n_D^{20}$1.4602 | N, 4.98<br>P, 11.01 | 5.52<br>9.90 |
| 12 | Acrolein | t-butylamine | (CH$_3$)$_3$NCH$_2$CH$_2$CHPO$_3$Et$_2$<br>\|<br>OH | 128–135°/25–50μ<br>$n_D^{20}$1.4580 | N, 5.24<br>P, 11.59 | 5.69<br>11.65 |
| 13 | Acrolein | di-n-butylamine | (n-C$_4$H$_9$)$_2$NCH$_2$CH$_2$CHPO$_3$Et$_2$<br>\|<br>OH | 135–155°/20–45μ<br>$n_D^{20}$1.4632 | N, 4.33<br>P, 9.58 | 4.62<br>9.49 |
| 14 | Acrolein | diethylamine | (C$_2$H$_5$)$_2$NCH$_2$CH$_2$CHPO$_3$(CH$_2$C$_6$H$_5$)$_2$<br>\|<br>OH | 150–156°/18–37μ<br>$n_D^{23}$1.5402 | N, 3.58<br>P, 7.91 | 3.06<br>6.46 |

| Ex. No. | Product Name |
|---|---|
| 10 | Phosphonic acid, [3-(diethylamino)-1-hydroxypropyl]-, diethyl ester |
| 11 | Phosphonic acid, diethyl ester, [1-hydroxy-3-(tert-pentylamino)propyl]-, |

TABLE II-continued

| | |
|---|---|
| 12 | Phosphonic acid, [3-(tert-butylamino)-1-hydroxypropyl]-, diethyl ester |
| 13 | Phosphonic acid, [3-(dibutylamino)-1-hydroxypropyl]-, diethyl ester |
| 14 | Phosphonic acid, dibenzyl ester, [3-(diethylamino)-1-hydroxypropyl]-, |

EXAMPLE 15

In a first step, a mixture was prepared by adding, in order, with stirring and cooling below 30° C., 15.2 ml (0.100 mole) diethyl malonate, 100 ml benzene as a solvent, 1 ml triethylamine, as a catalyst and 6.7 ml acrolein. In a second step, after being allowed to stand overnight, 12.9 ml (0.100 mole) diethyl phosphite was added, followed by sodium ethoxide/ethanol as catalyst. After standing an additional six days, the mixture was rotoevaporated to remove the benzene solvent, and the oily residue was distilled partially in the Smith still, product being collected at a wall temperature of 130°–153°/25–30μ. The distillate (7.5 g) contained 9.01% phosphorus; the calculated content for $C_{14}H_{27}O_8P$ is 8.74%. The residual oil (8.8 g) was also very largely the desired compound malonic acid, diethyl ester, [alpha-[3-(diethoxyphosphinyl)-3-hydroxypropyl]].

EXAMPLE 16

In a first step, a solution of 100 ml methanol containing 1 ml of sodium methoxide (25% in methanol) as a catalyst was stirred and cooled in an ice bath, then a solution of 6.7 ml acrolein (0.100 mole) in 30 ml methanol was added dropwise slowly to control the exotherm from 3° C. to 11° C. In a second step, 9.2 ml of dimethyl phosphite was added thereto. After 4 days, the solvent was removed and the crude oil was distilled in the Smith still at 120°–130°/45–50μ, giving 8.5 g (42% yield) of the product phosphonic acid, dimethyl ester, 1-hydroxy-3-methoxypropyl-; $n_D^{20} = 1.4564$. The product contained 16.20% phosphorus, $C_6H_{15}O_5P$ requiring 15.63% P.

EXAMPLE 17

The post-emergence herbicidal activity of some of the various compounds of this invention was demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annular plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm² absolute. The atomizer contains 6 ml. of a solution or suspension of the chemical. In that 6 ml., is an amount of a cyclohexanone emulsifying agent mixture to give a spray solution or suspension which contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Table III is as follows:

| Plant Response | Index |
|---|---|
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
|---|---|
| A - Canada Thistle* | G - Yellow Nutsedge* |
| B - Cocklebur | H - Quackgrass* |
| C - Velvetleaf | I - Johnsongrass* |
| D - Morningglory | J - Downy Brome |
| E - Lambsquarters | K - Barnyardgrass |
| F - Smartweed | |

*Established from vegetative propagules.

TABLE III

| Compound of Example No. | WAT | kg/h | A | B | C | D | E | F | G | H | I | J | K |
|---|---|---|---|---|---|---|---|---|---|---|---|---|---|
| 1 | 2 | 11.2 | 0 | 0 | 0 | 0 | 0 | 0 | 0 | 0 | 0 | 0 | 0 |
| | 2 | 56.0 | 4 | 2 | 3 | 3 | 4 | 4 | 0 | 2 | 2 | 1 | 2 |
| 2 | 2 | 11.2 | 0 | 0 | 0 | 0 | 0 | 0 | 0 | 0 | 0 | 0 | 0 |
| | 2 | 56.0 | 1 | 2 | 1 | 2 | 3 | 2 | 0 | 0 | 1 | 1 | 1 |
| 3 | 2 | 11.2 | — | 0 | 0 | 0 | 0 | 0 | 0 | 0 | 0 | 0 | 0 |
| | 2 | 56.0 | 1 | 2 | 2 | 2 | 3 | 4 | 0 | 0 | 0 | 1 | 2 |
| 4 | 2 | 11.2 | — | 0 | 0 | 0 | 0 | 0 | 0 | 0 | 0 | 0 | 0 |
| | 2 | 56.0 | 0 | 1 | 0 | 1 | 3 | 1 | 0 | 0 | 0 | 0 | 0 |
| 5 | 2 | 11.2 | 0 | 0 | 0 | 0 | 0 | — | 0 | 0 | 0 | 0 | 0 |
| | 2 | 56.0 | 0 | 2 | 1 | 1 | 2 | 1 | 0 | 0 | 0 | 0 | 0 |
| 6 | 2 | 11.2 | 0 | 0 | 0 | 0 | 1 | 0 | 0 | 0 | 0 | 0 | 0 |
| 7 | 2 | 11.2 | 0 | 0 | 0 | 2 | 3 | 1 | 0 | 0 | 0 | 0 | 0 |

TABLE III-continued

| Compound of Example No. | WAT | kg/h | A | B | C | D | E | F | G | H | I | J | K |
|---|---|---|---|---|---|---|---|---|---|---|---|---|---|
| 8 | 2 | 11.2 | 0 | 0 | 0 | 0 | 0 | 0 | 0 | 0 | 0 | 0 | 0 |
|  | 2 | 28.0 | 0 | 1 | 0 | 0 | 1 | 0 | 0 | 0 | 0 | 1 | 1 |
| 9 | 2 | 11.2 | 0 | 0 | 0 | 0 | 0 | 0 | 0 | 0 | 0 | 0 | 0 |
|  | 2 | 56.0 | 1 | 1 | 1 | 1 | 1 | 1 | 0 | 0 | 0 | 0 | 1 |
| 10 | 2 | 11.2 | 0 | 0 | 0 | 0 | 0 | 0 | 0 | 0 | 1 | 0 | 0 |
|  | 2 | 56.0 | 0 | 1 | 2 | 1 | 2 | 1 | 0 | 0 | 0 | 1 | 0 |
| 11 | 2 | 11.2 | 0 | 0 | 0 | 0 | 0 | 0 | 0 | 0 | 0 | 0 | 0 |
|  | 2 | 56.0 | 0 | 1 | 0 | 0 | 0 | 1 | 0 | 0 | 1 | 0 | 2 |
| 12 | 2 | 11.2 | 0 | 0 | 0 | 0 | 0 | 0 | 0 | 0 | 0 | 0 | 0 |
|  | 2 | 56.0 | 0 | 1 | 1 | 0 | 2 | 1 | 0 | 0 | 0 | 1 | 1 |
| 13 | 2 | 11.2 | 0 | 0 | 0 | 1 | — | 0 | 0 | 0 | 0 | 0 | 0 |
|  | 2 | 56.0 | 2 | 2 | 2 | 2 | 3 | 3 | 3 | 1 | 1 | 1 | 3 |
| 14 | 2 | 11.2 | 0 | 0 | 0 | 0 | 0 | 0 | 0 | 0 | 0 | 0 | 0 |
|  | 2 | 56.0 | 0 | 1 | 2 | 1 | 1 | 0 | 0 | 0 | 0 | 0 | 0 |
| 15 | 2 | 11.2 | — | 1 | 0 | 0 | 0 | 0 | 0 | 0 | 0 | 0 | 0 |
|  | 2 | 56.0 | 4 | 1 | 1 | 0 | 2 | 0 | 0 | 0 | 0 | 1 | 1 |
| 16 | 2 | 11.2 | 0 | 0 | 0 | 0 | 4 | — | 0 | 0 | 0 | 0 | 0 |
|  | 2 | 56.0 | 0 | 1 | 0 | 1 | 1 | 1 | 0 | 0 | 0 | 0 | 0 |

—Indicates species of plant absent during test

From the test results presented in Table III, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor such as ethanol mercaptan, sodium thiosulfate, dodecylmono or dimercaptan or anti-foaming agent such as a dimethylpolysiloxane, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

The following list gives some specific herbicidal compositions of this invention. It is to be realized that the solvents and surfactants are interchangeable in the composition.

| | | |
|---|---|---|
| 1. | Phosphonic acid, diethyl ester, [1-hydroxy-3-(pentylthio)-propyl]-, | 5 parts |
| | Methanol | 95 parts |
| 2. | Phosphonic acid, dimethyl ester, 1-hydroxy-3-methoxypropyl-, | 95 parts |
| | Ethoxylated nonyl phenol | 5 parts |
| 3. | Phosphonic acid, diethyl ester, [1-hydroxy-3-(heptylthio)propyl]-, | 90 parts |
| | Ethoxylated octyl phenol | 10 parts |
| 4. | Phosphonic acid, diethyl ester, [1-hydroxy-2-methyl-3-(propylthio)-propyl]-, | 90 parts |
| | Chloroform | 5 parts |
| | Ethoxylated dinonyl phenol | 5 parts |
| 5. | Phosphonic acid, diethyl ester, [1-hydroxy-3-(2-hydroxy-ethylthio)-propyl]-, | 75 parts |
| | Ethoxylated oleyl alcohol | 25 parts |
| 6. | Phosphonic acid, diethyl ester, [1-hydroxy-3-(isopropylthio)-propyl]-, | 35 parts |
| | Xylene | 55 parts |
| | Ethoxylated cocoamine | 10 parts |
| 7. | Phosphonic acid, diethyl ester, [1-hydroxy-1-methyl-3-(propylthio)-propyl]-, | 75 parts |
| | Toluene | 20 parts |
| | Ethoxylated tallow amine | 5 parts |
| 8. | Phosphonic acid, [3-(ethylalmino)-1-hydroxy-1-methylpropyl]-, diethyl ester | 50 parts |
| | Dimethylformamide | 50 parts |
| 9. | Phosphonic acid, diethyl ester, 1-hydroxy-3-piperidinopropyl-, | 50 parts |
| | Monochlorobenzene | 45 parts |
| | Ethoxylated nonyl phenol | 3 parts |

-continued

| | | |
|---|---|---|
| | Isopropyl dodecylbenzene sulfonate | 2 parts |
| 10. | Phosphonic acid, [3-diethylamino)-1-hydroxypropyl]-, diethyl ester | 50 parts |
| | O—chlorotoluene | 40 parts |
| | Ethoxylated soybeanamine | 10 parts |
| 11. | Phosphonic acid, diethyl ester, [1-hydroxy-3-(tert-pentylamino)-propyl]-, | 50 parts |
| | Toluene | 40 parts |
| | Ethoxylated castor oil | 5 parts |
| | Triethanolamine dodecylbenzene sulfonate | 5 parts |
| 12. | Malonic acid, diethyl ester, [alpha-[3-(diethoxyphosphinyl)-3-hydroxy-propyl]]-, | 50 parts |
| | 1,1,1-Trichloroethane | 42 parts |
| | Ethoxylated nonyl phenol | 8 parts |
| 13. | Phosphonic acid, [3-tert-butylamino)-1-hydroxypropyl]-, diethyl ester | 25 parts |
| | Chloroform | 75 parts |
| 14. | Phosphonic acid, [3-(dibutylamino)-1-hydroxypropyl]-, diethyl ester | 25 parts |
| | Chloroform | 70 parts |
| | Ethoxylated tallow amine | 5 parts |
| 15. | Phosphonic acid, diethyl ester, [1-hydroxy-3-(pentylthio)-propyl]-, | 25 parts |
| | 1,1,1-Trichloroethane | 74 parts |
| | Ethoxylated oleyl alcohol | 1 part |
| 16. | Phosphonic acid, diethyl ester, [1-hydroxy-3-(phenylthio)propyl]-, | 25 parts |
| | Chloroform | 68 parts |
| | Ethoxylated dinonyl phenol | 7 parts |
| 17. | Phosphonic acid, dibenzyl ester, [3-(diethylamino)-1-hydroxypropyl]-, | 10 parts |
| | Chloroform | 90 parts |
| 18. | Phosphonic acid, dimethyl ester, 1-hydroxy-3-methoxypropyl-, | 10 parts |
| | Xylene | 80 parts |
| | Polyoxypropylene - polyoxyethylene block copolymer | 10 parts |
| 19. | Phosphonic acid, diethyl ester, [1-hydroxy-3-(heptylthio)propyl]-, | 10 parts |
| | Kerosene | 30 parts |
| | Xylene | 58 parts |
| | Polyoxyethylene (20) sorbitan-monolaurate | 2 parts |
| 20. | Phosphonic acid, diethyl ester, [1-hydroxy-2-methyl-3-(propylthio)-propyl]-, | 10 parts |
| | Ethyl acetate | 72 parts |
| | Polyoxyethylene sorbitan-monooleate | 18 parts |
| 21. | Phosphonic acid, diethyl ester, [1-hydroxy-3-(2-hydroxy-ethylthio)-propyl]-, | 5 parts |
| | Dimethylformamide | 95 parts |
| 22. | Phosphonic acid, diethyl ester, [1-hydroxy-3-(isopropylthio)-propyl]-, | 5 parts |
| | Monochlorobenzene | 90 parts |
| | Ethoxylated tallow amine | 5 parts |
| 23. | Phosphonic acid, diethyl ester, [1-hydroxy-1-methyl-3-(propylthio)-propyl]-, | 5 parts |
| | Toluene | 60 parts |
| | Ethanol | 34 parts |
| | Ethoxylated tallow amine | 1 part |
| 24. | Phosphonic acid, diethyl ester, [1-hydroxy-3-(pentylthio)-propyl]-, | 5 parts |
| | Xylene | 45 parts |
| | Isopropanol | 35 parts |
| | Ethoxylated cocoamine | 15 parts |

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 56.0 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

There are several methods for applying liquid compositions of this invention to emerged plants. Such methods include the use of wiper systems whereby the plant to be treated is contacted with an absorbent material containing the particular liquid composition, a portion of which is thereby released onto the plant upon contact therewith. Such wiper systems typically comprise a reservoir of the liquid composition into which a portion of the absorbent material is placed and is fed therethrough. Generally, substances employable as absorbent material include substances of any shape or form capable of absorbing the liquid composition and releasing a portion of the same upon contact with the plant. Typical absorbent materials include felt, foam rubber, cellulose, nylon, sponges, hemp, cotton, burlap, polyester over acrylic, combinations thereof and the like. Forms of absorbent material include rope, twine, string, cloths, carpets, combinations thereof and the like. These forms may be assembled in any manner desired including a pipe rope wick, a wedge rope wick, a multi-rope wick and the like.

In another application method, liquid compositions may be selectively applied to weeds by the use of recirculating sprayer systems wherein the recirculating spray unit is mounted on a reactor or high clearance mobile equipment and the spray is directed horizontally onto the weeds growing over a crop. Spray not intercepted by the weeds is collected in a recovery chamber before contacting the crop and is reused. Roller applications may also be employed to apply liquid compositions to weeds growing over a crop.

In yet another application method, shielded applicators may be employed to direct the liquid composition in the form of a spray onto the weeds while effectively shielding the crops from the spray.

These and other application methods for selectively applying liquid compositions to weeds are discussed in detail in Innovative Methods of Post-Emergence Weed Control, McWhorter C. G., Southern Weed Science Society, 33rd Annual Meeting Proceedings, Jan. 15–17, 1980; Auburn University Printing Service, Auburn, Ala. United States, the teachings of which are incorporated herein by reference in their entirety.

Another method of applying liquid compositions of this invention to plants includes controlled droplet application which is also known as the ultra low-volume chemical application. Controlled droplet application involves the production of uniform or nearly uniform spray drops of a predetermined size and the conveyance of these drops with negligible evaporation to a spray target. In particular, this method comprises feeding spray solutions to a rotary atomizer comprising a small disk with serrated edges that disperses liquid into droplets as the disk spins. Different droplet sizes are produced by changing solution flow rates to the spinning disk or changing the speed of rotation of the disk.

The aforementioned and other methods for applying liquid compositions to plants are discussed in detail in "Rope Wick Applicator—Tool With A Future", Dale, James E., pp. 3–4, "The Recirculating Sprayer and Roundup ® Herbicide", Derting, Claude W., pp. 5–7, and "C.D.A. Herbicide Application", McGarvey, Frank X., *Weeds Today,* Volume 11, Number 2, pp. 8–9, Late Spring, 1980, 309 W. Clark St., Champaign, Ill., the teachings of which are incorporated herein by reference in their entirety.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. An α-hydroxy phosphonate compound of the formula

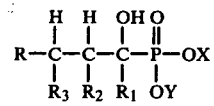

wherein X and Y are each independently selected from the group consisting of lower alkyl or benzyl; $R_1$, $R_2$ and $R_3$ are each independently selected from the group consisting of hydrogen, lower alkyl; R is a —Z—$R_4$ group wherein Z is oxygen or sulfur, and $R_4$ is lower alkyl, lower alkanol, aryl or R is piperidinyl or,

wherein —Z' is nitrogen, and $R_5$ is lower alkyl, or lower alkoxyalkylloweralkyl and $R_6$ is lower alkyl or hydrogen.

2. A compound of claim 1, wherein $R_1$, $R_2$ and $R_3$ are each hydrogen.

3. A compound of claim 2, wherein X and Y are the same group.

4. A compound of claim 3, wherein X and Y are both methyl, ethyl, or $CH_2C_6H_5$.

5. A compound of claim 4, wherein R is —Z—$R_4$ wherein Z is oxygen or sulfur and $R_4$ is lower alkyl, aryl or lower alkanol.

6. A compound of claim 5, wherein Z is sulfur and $R_4$ is pentyl, benzyl, heptyl, hydroxyethyl, isopropyl, n-propyl and phenyl.

7. A compound of claim 5, wherein Z' is nitrogen and $R_5$ and $R_6$ are each independently hydrogen, ethyl, t-butyl, t-pentyl and n-butyl.

8. A compound of claim 5, wherein Z is oxygen and $R_4$ is methyl.

9. A compound of claim 3, wherein R is piperidinyl.

10. A compound of claim 4, wherein R is $N(C_2H_5)_2$.

* * * * *